United States Patent
Mazaheri

(10) Patent No.: US 9,956,230 B2
(45) Date of Patent: May 1, 2018

(54) METHOD FOR VISUAL ENHANCEMENT AND POST PROCEDURE TREATMENT PROTOCOL

(71) Applicant: Michael Mehrdad Mazaheri, Richardson, TX (US)

(72) Inventor: Michael Mehrdad Mazaheri, Richardson, TX (US)

(*) Notice: Subject to any disclaimer, the term of this patent is extended or adjusted under 35 U.S.C. 154(b) by 264 days.

(21) Appl. No.: 14/537,559

(22) Filed: Nov. 10, 2014

(65) Prior Publication Data

US 2015/0065473 A1 Mar. 5, 2015

Related U.S. Application Data

(63) Continuation-in-part of application No. 11/253,373, filed on Oct. 19, 2005, now Pat. No. 9,192,517.

(51) Int. Cl.
| | |
|---|---|
| *A61B 17/00* | (2006.01) |
| *A61K 31/56* | (2006.01) |
| *A61K 9/00* | (2006.01) |
| *A61F 9/008* | (2006.01) |

(52) U.S. Cl.
CPC .............. *A61K 31/56* (2013.01); *A61F 9/008* (2013.01); *A61F 9/00804* (2013.01); *A61K 9/0048* (2013.01); *A61F 2009/00872* (2013.01)

(58) Field of Classification Search
CPC ....... A61K 31/56; A61K 9/0048; A61F 9/008; A61F 9/00804; A61F 2009/00872
USPC ................................................. 606/2; 607/88
See application file for complete search history.

(56) References Cited

U.S. PATENT DOCUMENTS

| | | | |
|---|---|---|---|
| 5,658,303 | A | 8/1997 | Koepnick |
| 5,934,285 | A | 8/1999 | Kritzinger et al. |
| 5,935,140 | A | 8/1999 | Buratto |
| 5,984,916 | A | 11/1999 | Lai |
| 5,993,441 | A | 11/1999 | Muller et al. |
| 6,293,938 | B1 | 9/2001 | Muller et al. |
| 6,312,439 | B1 | 11/2001 | Gordon |
| 6,740,078 | B2 | 5/2004 | Tamayo |
| 6,793,654 | B2 | 9/2004 | Lemberg |
| 6,843,787 | B2 | 1/2005 | Ruiz |
| 6,926,710 | B2 | 8/2005 | Cox et al. |
| 7,090,696 | B2 | 8/2006 | Shahinpoor et al. |
| 7,232,436 | B2 | 6/2007 | Bille |
| 2001/0016733 | A1 | 8/2001 | Frey et al. |
| 2002/0049428 | A1 | 4/2002 | Bruce |
| 2002/0154270 | A1 | 10/2002 | Halpern et al. |
| 2003/0009159 | A1 | 1/2003 | Clapham et al. |
| 2004/0054356 | A1 | 3/2004 | Odrich et al. |
| 2005/0149006 | A1 | 7/2005 | Peyman |
| 2005/0171515 | A1 | 8/2005 | Chernyak |
| 2012/0310141 | A1* | 12/2012 | Kornfield ................ A61F 9/008 604/20 |

* cited by examiner

*Primary Examiner* — Aaron Roane

(57) ABSTRACT

A new and novel method for determining post procedural treatment is disclosed herein. In one embodiment, a method for a treating a patient following a surgical procedure on at least one eye comprises determining a depth at which the surgical procedure is to be performed or was performed, and providing instructions for administering medication for a length of time to the at least one eye of the patient, the length of time based at least in part upon the depth.

23 Claims, 9 Drawing Sheets

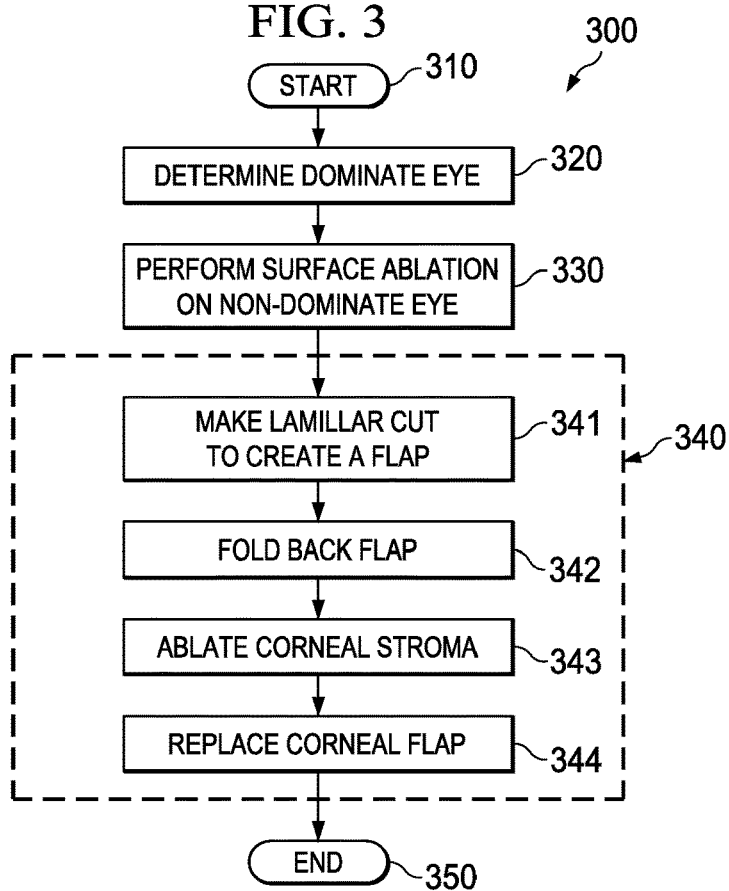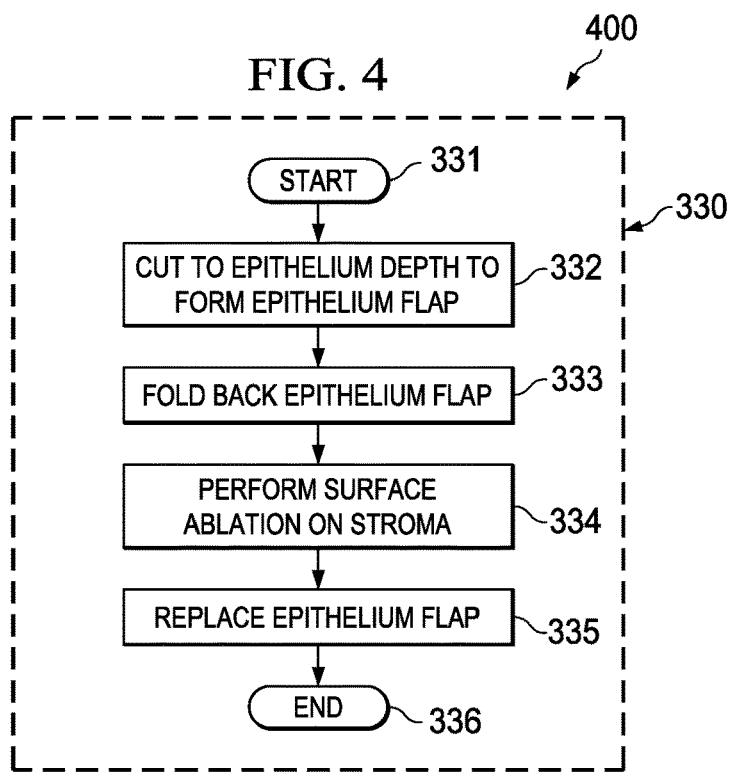

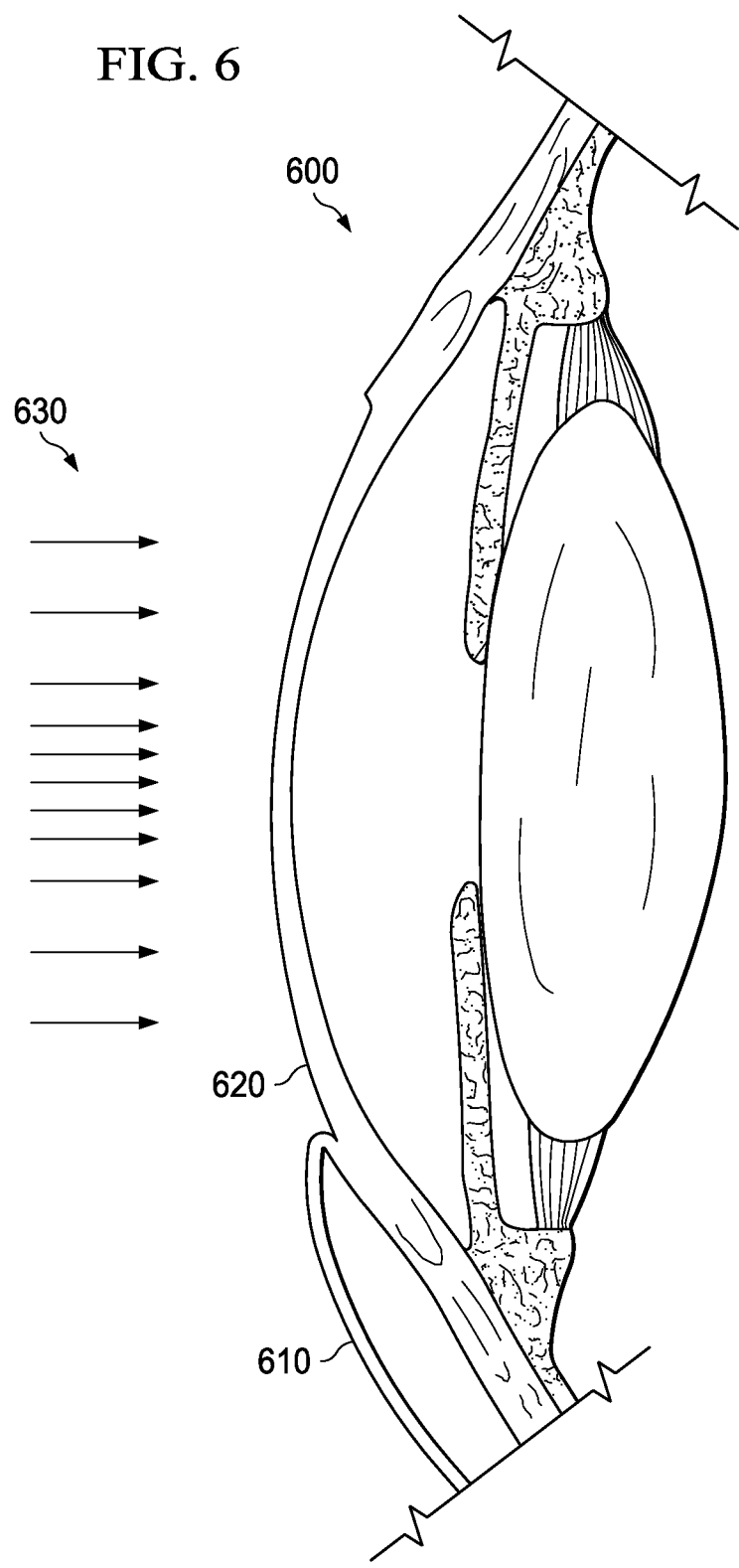

FIG. 8
Next Generation Advanced PRK Protocol

| Ablation Depth (Microns) | Treatment Time Post Surgery (Months) | Lotemax Week(s) | 1 gtt: |
|---|---|---|---|
| 20 | 2.5 | 3 | QID |
| | | 3 | TID |
| | | 3 | BID |
| | | 1 | QD |
| 30 | 3 | 3 | QID |
| | | 3 | TID |
| | | 3 | BID |
| | | 3 | QD |
| 40 | 4 | 4 | QID |
| | | 4 | TID |
| | | 4 | BID |
| | | 4 | QD |
| 50 | 5 | 5 | QID |
| | | 5 | TID |
| | | 5 | BID |
| | | 5 | QD |
| 60-70 | 6 | 6 | QID |
| | | 6 | TID |
| | | 6 | BID |
| | | 6 | QD |
| 70-80 | 7 | 7 | QID |
| | | 7 | TID |
| | | 7 | BID |
| | | 7 | QD |
| 80-90 | 8 | 8 | QID |
| | | 8 | TID |
| | | 8 | BID |
| | | 8 | QD |

If patient's age is over 55, subtract 1 week from treatment. If patient's age is under 27, add 1 week to treatment.

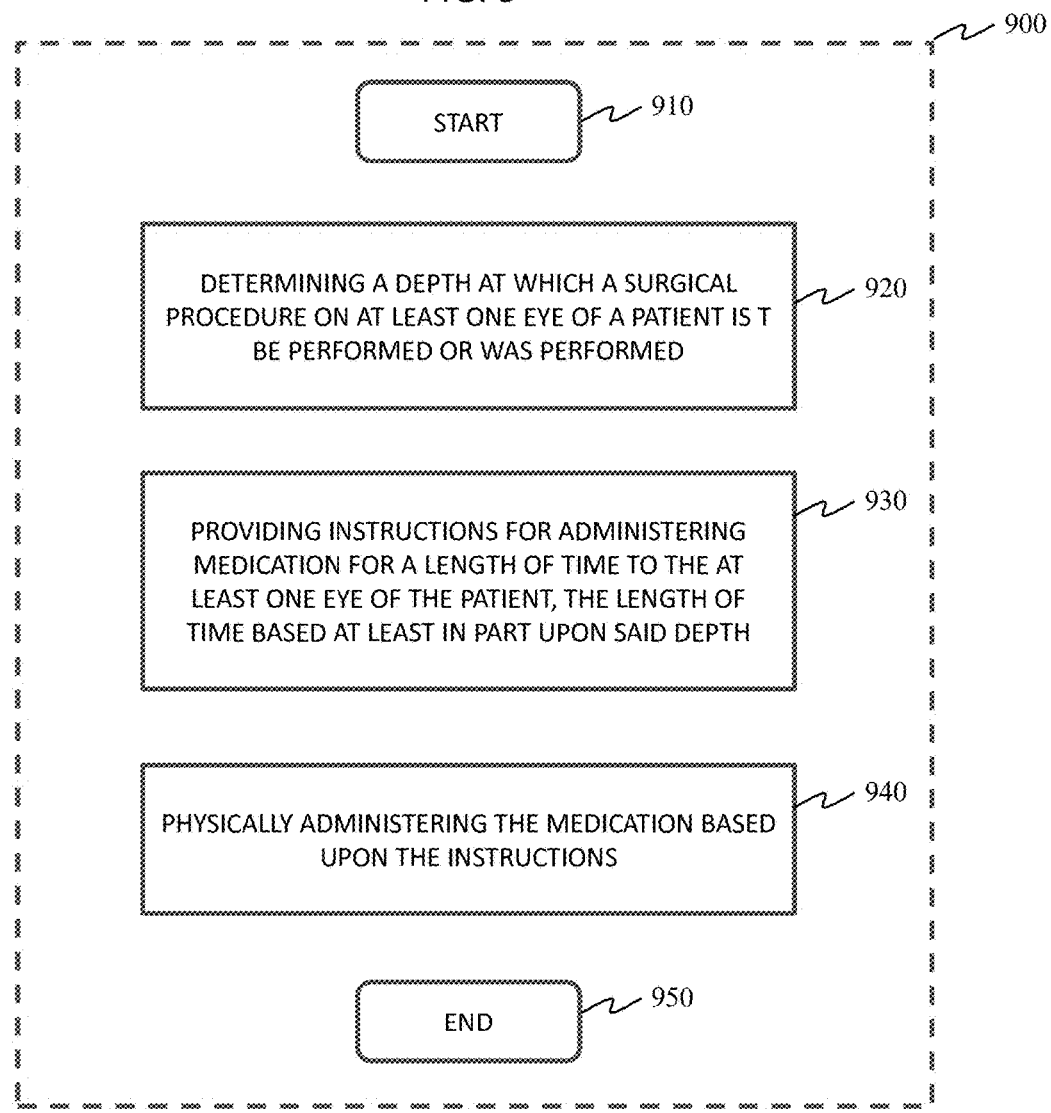

METHOD FOR VISUAL ENHANCEMENT AND POST PROCEDURE TREATMENT PROTOCOL

CROSS REFERENCE TO RELATED APPLICATIONS

This application is a continuation-in-part of U.S. application Ser. No. 11/253,373 filed on Oct. 19, 2005, entitled "Mazaheri Lasik Method for Visual Enhancement," the entire contents of which are incorporated herein by reference.

TECHNICAL FIELD

The present disclosure is directed, in general, to a surgical procedure and post-operative treatment and, more particularly, to customized post-operative treatment protocol following a surgical procedure to improve the visual acuity of a patient.

BACKGROUND

There are a number of types of photorefractive surgical procedures now being used for vision correction. Included among these procedures is LASIK (Laser-Assisted In Situ Keratomileusis). LASIK is a procedure used to permanently change the shape of the cornea with an Excimer laser. A flap is cut in the cornea and folded back revealing the stroma, which is the middlesection of the cornea. Pulses from a computer-controlled Eximer laser are used to ablate or vaporize a portion of the interior of the stroma and reshape the corneal tissue. The flap is then replaced over the reshaped area to conform to the new corneal shape.

Some patients, however, are not suitable candidates for LASIK. Those patients that have extremely thin corneas are better served using a procedure other than LASIK. Advanced surface ablations techniques provide a suitable alternative in such cases. These techniques involve the removal of the very surface layer of the cornea, known as the epithelium, and lasering the exposed corneal bed. This keeps the laser from ablating or vaporizing too deep into the tissue of the cornea and reduces the risk of ectasia, or de-stabilization of the cornea.

Both LASIK and the various surface ablation techniques can be grouped under the general umbrella of laser eye surgery, but each is a little different with respect to their advantages and disadvantages. The great advantage of LASIK over a surface ablation technique, is that, as soon as the flap created during the LASIK procedure is replaced, the cornea begins to heal and will naturally seal itself to the rest of the cornea. This greatly speeds the overall healing process when compared to surface ablation techniques, which leaves the reshaped area generally more exposed or open. With surface ablation, improvement is more gradual and the eye may take a few days or even a month or two to stabilize. In general, most surgeons prefer LASIK except for patients with thin corneas, in which case a surface ablation technique is preferred. Patient satisfaction is another reason surgeons prefer LASIK, because the patient can quickly see clearly and his or her anxiety is significantly reduced.

Several potential problems are inherent in LASIK. The three most common problems are: (1) under correction, where not enough tissue is removed during the procedure; (2) over correction, where too much tissue is removed during the procedure; and (3) wrinkling of the corneal flap, where a small fold or wrinkle occurs during replacement which causes a small blurry area in the patients vision. In most cases each of these problems can be easily corrected with a second surgical procedure. Of course, if the under or over correction is very slight, the surgeon will most likely advise against any attempt to refine the patient's vision any further. In fact, many recipients of laser eye surgery, although they may never achieve normal vision, view the procedure as a success if they are able to achieve a significant reduction in their corrective-lens prescription.

In addition to the more common surgical type of problems listed above, there is also a potential for certain side effects to occur with respect to LASIK. Such side effects include dryness, blurred vision, halos around lights, increased light sensitivity, diffuse lamellar keratitis, torn flaps, incomplete flaps, and even double vision. There is also a chance that damage or scarring to the cornea can occur with the resultant partial or complete loss of vision.

Accordingly, what is needed in the art to overcome the problems set forth above is a procedure that combines the benefits of LASIK with a surface ablation technique along with an appropriate post-operative treatment.

SUMMARY

The present disclosure provides methods for performing refractive correction on a patient's eyes and methods for treating a patient following a surgical procedure, such as refractive correction, on at least one eye. In one embodiment, a method for a treating a patient following a surgical procedure on at least one eye comprises determining a depth at which the surgical procedure is to be performed or was performed, and providing instructions for administering medication for a length of time to the at least one eye of the patient, the length of time based at least in part upon the depth.

In another embodiment, a method for treating a patient needing correction on at least one eye comprises performing a surface ablation corrective procedure on a corneal surface of one or more of the patient's eyes. The method further includes determining a depth at which the performing the surface ablation is to be performed or was performed, and providing instructions for administering medication for a length of time to the one or more of the patient's eyes, the length of time based at least in part upon said depth.

In yet another embodiment there is disclosed a treatment protocol for a patient following a surgical procedure on at least one eye at a depth. The treatment protocol comprises determining a length of time for post-operative treatment based on the depth, the length of time including at least a first, second, third, and fourth interval; determining a medicine dosage and frequency for each of the first, second, third, and fourth intervals based on the depth; and instructing the patient to administer the medication according to the determining medicine dosage and medicine frequency. The medicine frequency may vary and decrease for each of the first, second, third, and fourth time intervals.

BRIEF DESCRIPTION OF THE DRAWINGS

For a more complete understanding of the disclosure, reference is now made to the following descriptions taken in conjunction with the accompanying drawing, in which:

FIG. 3 illustrates a flow chart of an embodiment of a method for performing refractive correction of a patient's eyesight in accordance with the present disclosure;

FIG. 4 illustrates a flow chart of the perform surface ablation of non-dominate eye step, as illustrated in FIG. 3, wherein an epithelium flap is formed before surface ablation;

FIG. 6 illustrates a cross-sectional view of a patient's non-dominant eye where an epithelium flap is formed prior to performing surface ablation in accordance with the present disclosure;

FIG. 8 is a chart illustrating an example of post-procedural treatment protocol in accordance with the present disclosure.

FIG. 9 illustrates a flow chart of a method for treating a patient, as further discussed above in FIG. 8.

DETAILED DESCRIPTION

Figure 1:
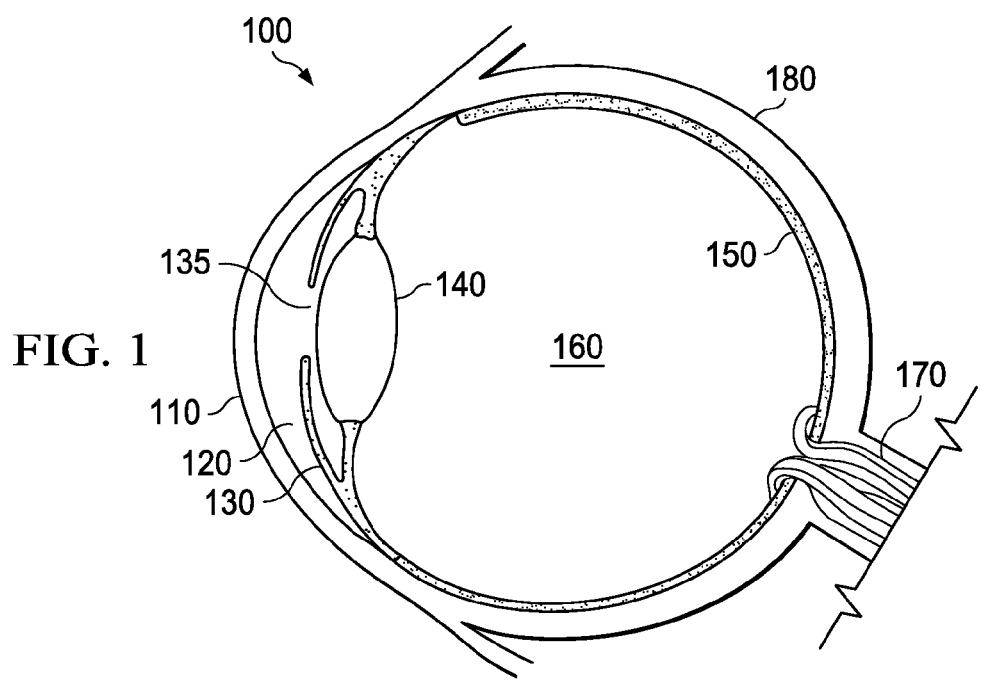
FIG. 1 illustrates a cross sectional view of a human eye showing its major components.

Referring initially to FIG. 1, illustrated is a cross sectional view of a human eye 100 showing its major components. As light enters the eye it first passes through a lubricating tear film that coats the cornea 110, which covers the front of the eye 100 and helps to focus incoming light. After light passes through the cornea 110 it travels through a clear, watery fluid called the aqueous humor 120. The aqueous humor 120 circulates throughout the front part of the eye 100, maintaining a constant pressure inside the eye 100. The amount of light permitted to enter the eye 100 is controlled by the iris 130, which is the colored part of the eye. As light conditions change, the iris 130 may dilate to make the pupil 135 bigger or constrict to make the pupil 135 smaller to allow more or less light into the eye 100. After light travels through the pupil 135, it must pass through the lens 140. Much like the lens of a camera, the human lens 140 is responsible for focusing light by changing its shape to focus on nearby or distant objects. After the light is focused by the lens 140, the light passes through the center of the eye 100 on its way to the retina 150. The center of the eye 100 is filled with a clear, jelly-like substance called the vitreous 160. The retina 150 is a thin, light-sensitive tissue lining the back of the eye 100 on which the light must be properly focused. The surface of the retina 150 must be flat, smooth, and in good working order to produce a clear image. At the back of the eye 100 is the optic nerve 170, which is a bundle of nerve fibers that carries visual information from the eye 100 to the brain. Protecting the inner workings of the eye 100 is a tough, fibrous tissue called the sclera 180. This is the white part of the eye 100.

Figure 2:
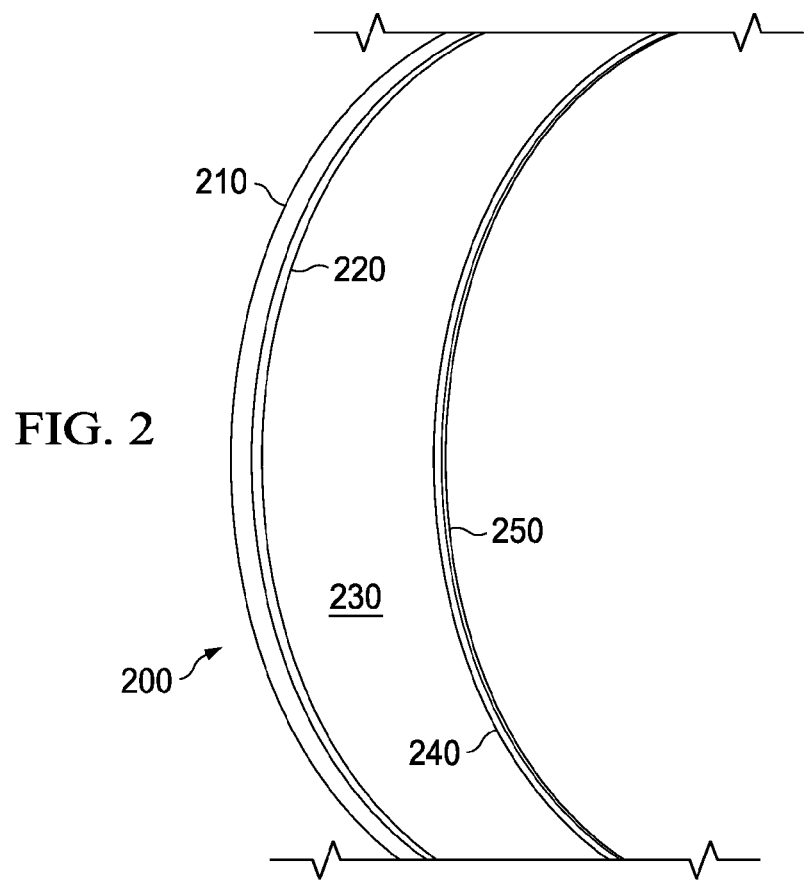
FIG. 2 illustrates a representational cross-sectional view of a cornea of an eye showing its layers.

Turning now to FIG. 2, illustrated is a representational cross-sectional view of a cornea 200 of an eye 100 showing its layers. As those of ordinary skill in the pertinent art will readily understand, neither the drawing nor the depicted layers are to scale. The purpose is to illustrate the relative positions of the various layers with respect to each other in order to facilitate an understanding of the present disclosure. The cornea 200 is a transparent, dome-shaped window covering the front of the eye 100 and is a powerful refracting surface, providing about two-thirds of the eye's 100 focusing power. Thus, the focal length of the eye 100 can be significantly changed by means of a surgical alteration of the shape of the cornea 200. The adult cornea 200 is about one-half a millimeter thick and is comprised of five layers: epithelium 210, Bowman's membrane 220, stroma 230, Descemet's membrane 240 and the endothelium 250.

The epithelium 210 is the cornea's 200 outermost region, comprising about ten percent of its thickness. It is about 5-6 cell layers thick and quickly regenerates when the cornea 200 is injured. If the injury penetrates more deeply into the cornea 200, it may result in scarring and leave opaque areas, causing the cornea 200 to lose its clarity and luster. Bowman's membrane 220 lies just beneath the epithelium 210 and, because is tough and difficult to penetrate, protects the cornea 200 from injury. Once injured, however, Bowman's membrane 220 can scar as it heals. If these scars are large and centrally located, some vision loss can occur.

Beneath Bowman's membrane 220 is the stroma 230, which makes up about ninety percent of the thickness of the cornea 200. The thickness of the stroma 230 offers the best opportunity to surgically improve a patient's vision. Beneath the stroma 230 is Descemet's membrane 240, a thin layer of very strong tissue that serves as a protective barrier against infection and injuries. Finally, underlying Descemet's membrane 240 is the endothelium 250, which is only one cell layer thick.

When an individual's eye 100 is focusing on an object, if the eye 100 is too short or the lens 140 is too flat or inflexible, the light entering the eye 100, particularly those from nearby objects, will not be focused by the time it strikes the retina 150. This is called farsightedness, or hypermetropia. In the case of eyeglass wearers, convex lenses are used to correct the problem. If the eye 100 is too long or the lens 140 is too spherical, the image of distant objects is brought to a focus in front of the retina 150 and is again out of focus. This condition is known as myopia and is corrected, in the case of eyeglass wearers, by prescribing eyeglasses with concave lenses to cause a divergence of the light rays before they enter the eye 100.

To overcome these types of vision problems, the focal length of the eye 100 can be modified by surgically changing the shape of the eye. This is done by reshaping the cornea 110, usually with a laser although it can also be done using other techniques, such as making radial cuts with a knife. Several different types of surgical techniques for vision correction are well known, all of which have their own advantages and disadvantage. The present disclosure introduces a new and novel surgical technique that minimizes some of the disadvantages of these other techniques.

Turning now to FIG. 3, illustrated is a flow chart of an embodiment of a method 300 for performing refractive correction of a patient's eyesight in accordance with the present disclosure. The method commences with a start step 310. In a determine dominant eye step 320, the patient's dominant eye is determined, which also means that the non-dominant eye is determined. Of course, as will be readily understood by those skilled in the pertinent art, during the course of determining the patient's dominant and non-dominant eye other determinations are also being made with respect to the patient, including a determination of how much of a surgical correction can and needs to be made to improve the patient's vision.

In a perform surface ablation on non dominant eye step 330, a surface ablation corrective procedure is performed on the corneal surface of the patient's non-dominant eye. Such correction, for safety measures and at the option of the surgeon, may be an under correction in order to avoid any complications that could be caused by an over correction. While conducting the perform surface ablation on non-dominant eye step 330, the surgeon will also be able to make a more accurate assessment of whether the patient suffers from an epithelial or Bowman membrane disease that will impede healing or cause in-growth. As will be understood by those of ordinary skill in the pertinent art, a laser device will be used to perform the surface ablation on non-dominant eye step 330. Although present technology calls for the use of a laser device, it is the intent of the present disclosure to cover other now known or later discovered technologies by which the present disclosure may be implemented, even if such technologies do not use or contemplate the use of a laser device.

In a reshape corneal stroma of dominant eye 340, the stroma is reshaped to provide the requisite visual correction. This step includes, a make lamillar cut to create a flap step 341, wherein a micro-kerotome, or other cutting instrument, is used to make a lamillar circular incision in the corneal surface of the eye while leaving an edge attached to create a flap. This incision cuts through the epithelium 210 and Bowman's layer 220 and into the outer surface of the stroma 230. The flap is then folded back in a fold flap back step 342 to reveal the interior portion of the corneal stroma 230. In an ablate corneal stroma step 343, a portion of the stroma 230 is ablated to produce the desired vision correction. Of course, as will be understood by those skilled in the pertinent art, the ablation will most likely be done using a laser device, although the present disclosure is intended to be applicable to other ablation techniques, whether now known or subsequently discovered. If a laser device is being used, those skilled in the pertinent art will also understand that the laser device may one of several different types with different computer operating systems. After the surgeon has completed ablation of the stroma 230, the corneal flap is replaced by folding it back into place in a replace corneal flap step 344. The method concludes with an end step 350.

The forgoing method or procedure can be usefully employed to correct myopic vision as well as hypermetropia. The method can also be utilized to reshape the cornea to correct certain types of astigmatism. The described technique also has the added benefit of permitting the surgeon to enhance the refractive correction on the patient's dominant eye, which enhancement can be achieved by a further reshaping of the corneal stroma.

Turning now to FIG. 4, illustrated is a flow chart 400 of the perform surface ablation of non-dominate eye step 330, as illustrated in FIG. 3, wherein an epithelium flap is formed before the surface ablation. This procedure is identical to that illustrated in FIG. 3, except for the following described refinement to the perform surface ablation on non-dominant eye step 330. The perform surface ablation step on non-dominate eye step 330 includes a start step 331 followed by a cut to epithelium depth to form an epithelium flap step 332. Following the cut to epithelium depth to form epithelium flap step 332, in a fold back epithelium flap step 333, the epithelium flap is folded back to expose the surface of the corneal stroma. Then in a perform surface ablation on stroma step 334, surface ablation is performed on the stroma by the surgeon to effect a vision correction. Then in a replace epithelium flap step 335, the epithelium flap is folded back. This refinement of the perform surface ablation on the non-dominant eye step 330 concludes with an end step 336.

Figure 5:
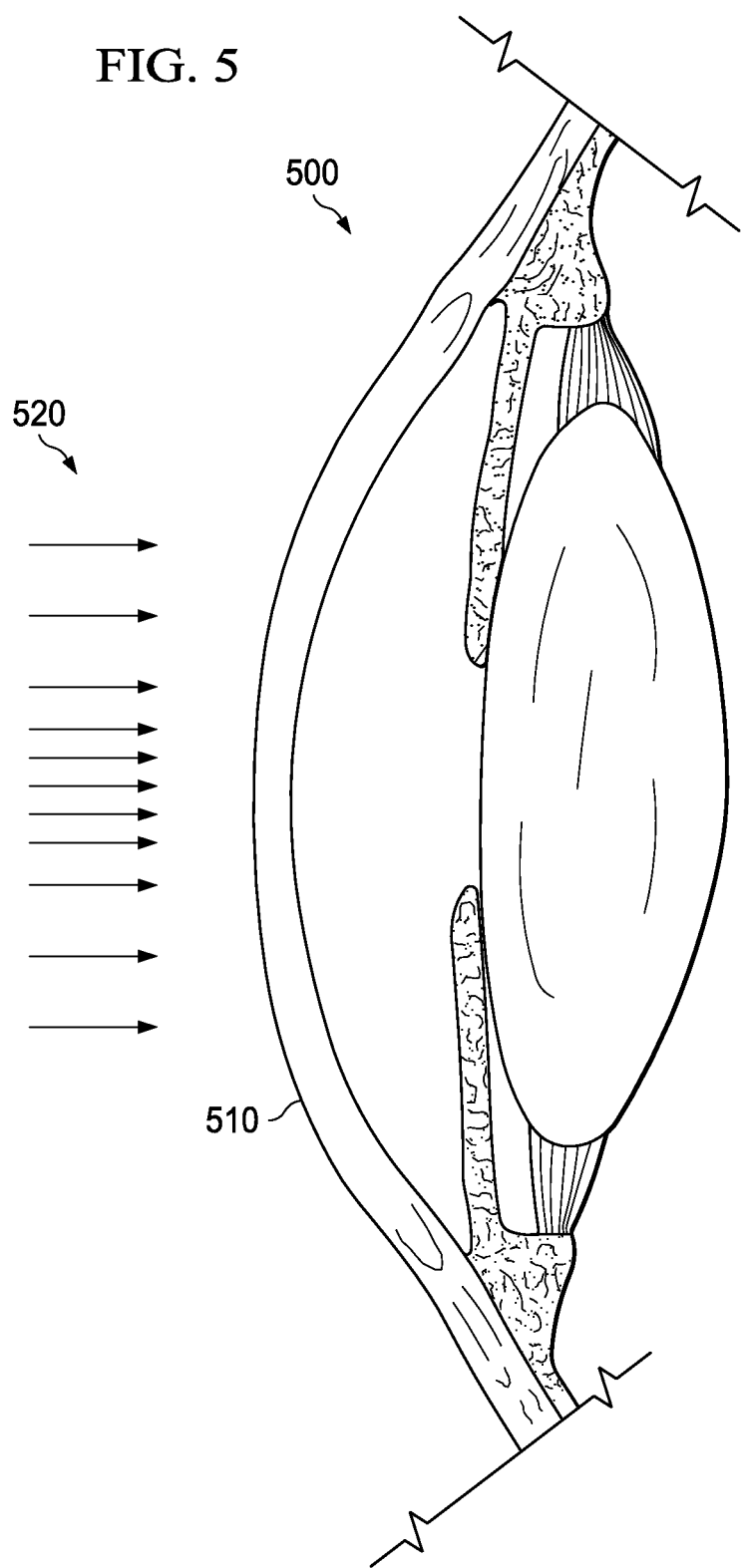
FIG. 5 illustrates a cross-sectional view of a patient's non-dominant eye on which surface ablation is performed in accordance with the present disclosure.

Turning now to FIG. 5, illustrates a cross-sectional view of a patient's non-dominant eye 500 on which surface ablation is performed. The cornea 510 of the non-dominant eye 500 is subjected to in-situ surface ablation to modify the curvature of the cornea 510 to a value determined by the surgeon. The ablation is performed with a laser device or any other method suitable for the removal of tissue with the parameters defined by the surgeon. In this procedure, the epithelium and Bowman's layer are removed.

Turning now to FIG. 6, illustrates a cross-sectional view of a patient's non-dominant eye 600 where an epithelium flap 610 is formed prior to performing surface ablation in accordance with the present disclosure. In this embodiment, a cut is made through the epithelium layer of the eye to form a flap 610. The flap 610 is folded back to expose the stroma surface 620. The stroma surface 620 is then subjected to in-situ surface ablation 630 to modify the curvature to a value determined by the surgeon. As noted previously, ablation is performed using a laser device or any other method suitable for the removal of tissue within the parameters defined by the surgeon. After completion of in-situ surface ablation 630 to modify the stroma surface 620, the epithelium flap 610 is replaced. In this procedure, the epithelium layer is retained.

Figure 7A:
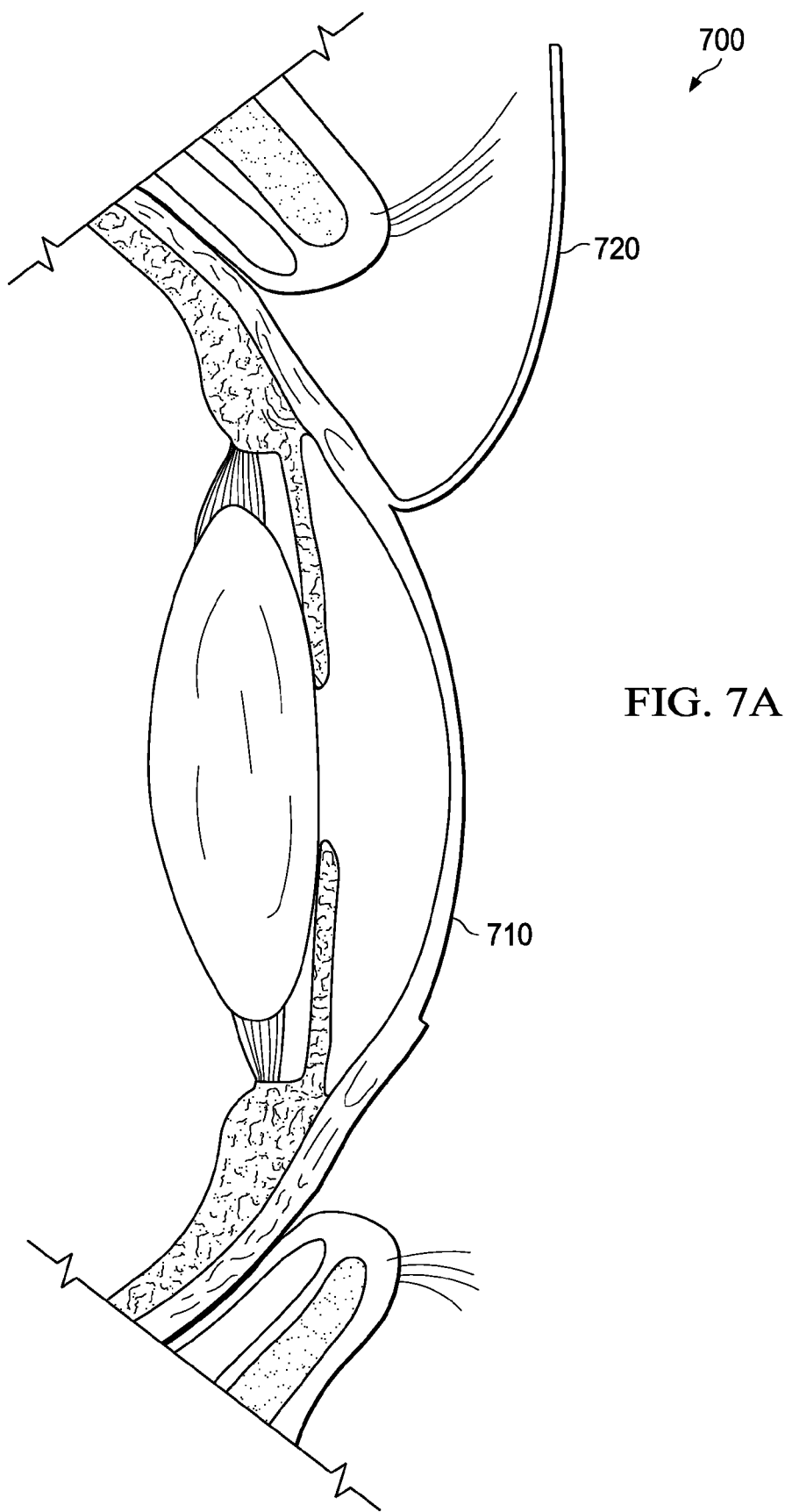
FIGS. 7A-7C illustrate the reshaping of a corneal stroma of a patient's dominant eye in accordance with the present disclosure.
Figure 7B:
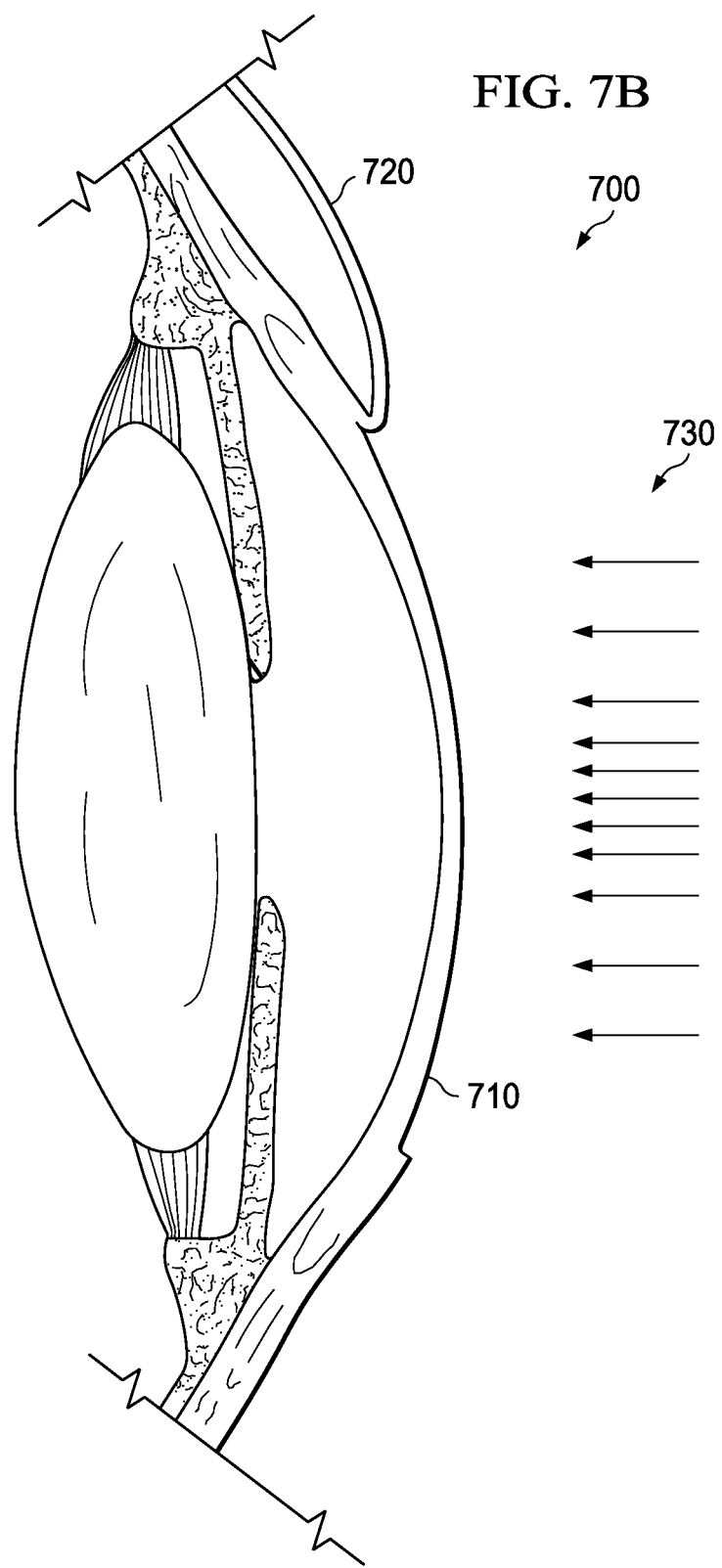
Figure 7C:
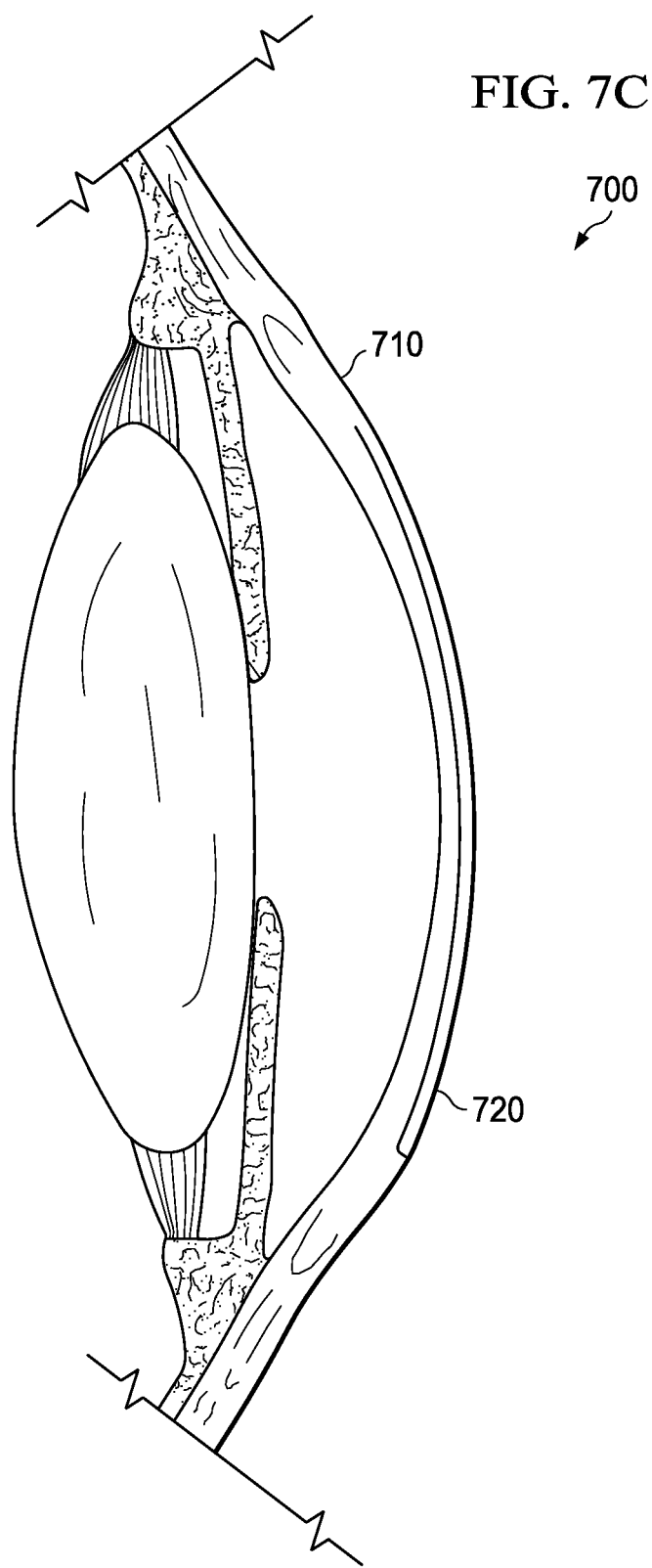

Turning now to FIGS. 7A-7C, illustrated is the reshaping of a corneal stroma 710 of a patient's dominant eye 700 in accordance with the present disclosure. The reshaping includes making a lamillar cut using a kerotome or other suitable surgical instrument in the surface of the cornea of the dominant eye 700 to create a flap 720. The flap 720 is then folded back to reveal the mid-section of the corneal stroma 710. The corneal stroma 720 is then subjected to ablation to modify the curvature to a value determined by the surgeon. Again, as previously noted, ablation is performed using a laser device or any other method suitable for the removal of tissue within the parameters defined by the surgeon. After ablating a portion of the corneal stroma 710, the flap 720, which includes both the epithelium and Bowman's layer, is replaced over the corneal stroma 710.

An advantage of the above-described technique is that the surgery can be productively enhanced. The healing of the dominant eye 700 is usually quite rapid. If the surgeon needs to enhance the correction, the flap 720 can be lifted again or cut anew and the shape of the interior portion of the corneal stroma 710 can be further refined.

FIG. 8 provides a chart illustrating an example of a post-operative (post op) treatment protocol that may be used following surgery. After surgery, an anti-inflammatory medication is often prescribed to be administered by drops into the treated eye, such as, for example, ophthalmic steroids. While traditional protocols included a general prescription amount of medication, the present disclosure provides a treatment protocol customized according to several factors, including, but not limited to, the patient's age, depth of treatment (e.g., cut) in the eye, and the time of administration of the medicine relative to the surgical procedure.

FIG. 8 illustrates one example of post-operative treatment protocol, wherein the length of post-operative treatment, medicine dosage and/or frequency are based on the depth at which a patient's eye is going to be or was treated, such as, for example, an ablation depth on an eye needing refractive correction. In certain embodiments the depth is determined prior to the procedure, for example by way of preparation, and in other embodiments is determined during the procedure itself. The procedure, among others covered, includes a surface ablation corrective procedure on a corneal surface of one or more of a patient's eyes. By customizing a treatment plan based on the depth (e.g., ablation depth), the outcome of the procedure, post-operative pain, and healing time are improved over traditional post-operative treatment protocols. For example, a patient with an ablation depth of 20 microns, might be prescribed ophthalmic steroids, such as LOTEMAX® eye drops, for a period of 2.5 months, or about 10 weeks after surgery. For the first three weeks, the prescription might call for 1 drop, four times per day. For the next three weeks, the prescription might call for 1 drop, three times per day. For the following three weeks, the prescription might call for 1 drop, twice per day, and the last week of treatment will be prescribed 1 drop, only once per day. However, if the ablation depth is deeper, such as 60-70 microns, the treatment protocol might be different, for example longer (e.g., for about 8 months after surgery). For the first 8 weeks, in this embodiment, the prescription might call for 1 drop, four times per day. For each week increment, the number of times per day for each drop might decrease by one until the final 8 weeks of treatment, during which the prescription will call for 1 drop, only once per day. In addition, for patients under 27 years of age, the surgeon may add 1 week of treatment for improved results. Similarly, for patients over 55 years of age, the surgeon may subtract 1 week from treatment.

While the foregoing treatment protocol illustrates one example of a treatment protocol prescribed after an eye surgery as described in the present disclosure, the customization of post-operative treatment protocols based on a treatment depth may be applied to other types of eye treatments and procedures. Further, as surgical and medical procedures continue to evolve and new medications are developed and improved, the amount of medication and treatment time may be adjusted accordingly.

Turning now to FIG. 9, illustrated is a flow chart 900 of a method for treating a patient, as further discussed above in FIG. 8. The method for treating a patient includes a start step 910 followed by a determining a depth at which a surgical procedure on at least one eye of a patient is to be performed or was performed step 920. Following the determining the depth step 920, in a step 930, instructions for administering medication for a length of time to the at least one eye of the patient are provided, the length of time based at least in part upon said depth. Thereafter, in a step 940, the medication is physically administered based upon the instructions. The process, in this embodiment, concludes with an end step 950.

While the example and description reference ophthalmic steroids, such as LOTEMAX® eye drops, other ophthalmic medications, both prescriptive and over the counter, may be used in conjunction with or as an alternative to of an ophthalmic steroid, according to the procedure performed on the eye.

Although the disclosed embodiments have been described in detail, those skilled in the pertinent art should understand that they various changes, substitutions and alterations may be made in addition to the details provided in the present disclosure without departing from the spirit and scope of the disclosure in its broadest form.

What is claimed is:

1. A method for a treating a patient, the method comprising:
   determining a depth at which a surgical procedure on at least one eye of a patient is to be performed or was performed;
   providing instructions for administering medication for a length of time to said at least one eye of said patient, said length of time based at least in part upon said depth; and
   physically administering the medication based upon the instructions.

2. The method according to claim 1, wherein said length of time includes a least a first interval, a second interval, a third interval, and a fourth interval, wherein each of said first, second, third, and fourth intervals includes at least one week.

3. The method according to claim 2, wherein providing instructions further includes providing instructions for administering medication for a medicine dosage or medicine frequency, said medicine dosage or medicine frequency based at least in part upon said depth.

4. The method according to claim 3, wherein said medicine dosage and said medicine frequency is defined for each of said first, second, third, and fourth intervals.

5. The method according to claim 3, wherein said medicine frequency for said first interval is four times per day.

6. The method according to claim 3, wherein said medicine frequency for said second interval is three times per day.

7. The method according to claim 3, wherein said medicine frequency for said third interval is two times per day.

8. The method according to claim 3, wherein said medicine frequency for said fourth interval is one time per day.

9. The method according to claim 1, wherein said medicine comprises an ophthalmic steroid.

10. The method according to claim 1, wherein said length of time increases as said depth increases.

11. A method for treating a patient following a surgical procedure on a patient needing correction on at least one eye, comprising:
    performing a surface ablation corrective procedure on a corneal surface of one or more of a patient's eyes;
    determining a depth at which said performing said surface ablation is to be performed or was performed;
    providing instructions for administering medication for a length of time to said one or more of said patient's eyes, said length of time based at least in part upon said depth; and
    physically administering the medication based upon the instructions.

12. The method according to claim 11, wherein said length of time includes a least a first interval, a second interval, a third interval, and a fourth interval, wherein each of said first, second, third, and fourth intervals includes at least one week.

13. The method according to claim 12, wherein providing instructions further includes providing instructions for administering medication for a medicine dosage or medicine frequency, said medicine dosage or medicine frequency based at least in part upon said depth.

14. The method according to claim 13, wherein said medicine dosage and said medicine frequency are defined for each of said first, second, third, and fourth intervals.

15. The method according to claim 13, wherein said medicine frequency for said first interval is four times per day.

16. The method according to claim 13, wherein said medicine frequency for said second interval is three times per day.

17. The method according to claim 13, wherein said medicine frequency for said third interval is two times per day.

18. The method according to claim 13, wherein said medicine frequency for said fourth interval is one time per day.

19. The method according to claim 11, wherein said medicine comprises an ophthalmic steroid.

20. The method according to claim 11, wherein said length of time increases as said depth increases.

21. A treatment protocol for a patient following a surgical procedure on at least one eye at a depth, comprising:

determining a length of time for post-operative treatment based on said depth, said length of time including at least a first, second, third, and fourth interval;

determining a medicine dosage and frequency for each of said first, second, third, and fourth intervals based on said depth;

instructing said patient to administer said medication according to said determining said length, medicine dosage and medicine frequency; and the patient physically administering the medication based upon the instructions.

22. The treatment protocol according to claim 21, wherein said medicine frequency for said first interval is four times per day, said medicine frequency for said second interval is three times per day, said medicine frequency for said third interval is two times per day, and said medicine frequency for said fourth interval is one time per day.

23. The treatment protocol according to claim 21, wherein said length of time increases as said depth increases.

* * * * *